United States Patent [19]

Katsura et al.

[11] Patent Number: 4,470,882
[45] Date of Patent: Sep. 11, 1984

[54] GAS LEAK DETECTOR

[75] Inventors: Masaki Katsura, Yokosuka; Mituo Harata, Kawasaki; Osamu Takikawa, Kamakura; Masayuki Shiratori, Kawasaki, all of Japan

[73] Assignee: Tokyo Shibaura Denki Kabushiki Kaisha, Kawasaki, Japan

[21] Appl. No.: 419,627

[22] Filed: Sep. 20, 1982

[30] Foreign Application Priority Data

Sep. 25, 1981 [JP] Japan ................. 56-150795

[51] Int. Cl.³ .................. G01N 27/46; G01N 7/10
[52] U.S. Cl. .................. 204/1 T; 204/427; 204/428
[58] Field of Search ........... 204/195 S, 429, 431, 204/424; 338/34; 252/464

[56] References Cited

U.S. PATENT DOCUMENTS

| 3,658,479 | 4/1972 | Heijne et al. | 23/254 E |
| 3,870,743 | 3/1975 | Ibing et al. | 260/465 C |
| 3,871,981 | 3/1975 | Flais et al. | 204/195 S |
| 3,936,794 | 2/1976 | Beaudoin et al. | 338/34 |
| 3,981,785 | 9/1976 | Sandler | 204/195 S |
| 4,059,628 | 11/1977 | Del Pesco et al. | 260/581 |
| 4,113,745 | 9/1978 | Strojny et al. | 260/346.7 S |
| 4,269,737 | 5/1981 | Grenoble et al. | 252/464 |

FOREIGN PATENT DOCUMENTS 54-146690 11/1979 Japan .
55-132947 10/1980 Japan .

Primary Examiner—T. Tung
Assistant Examiner—Nathan Thane
Attorney, Agent, or Firm—Schwartz, Jeffery, Schwaab, Mack, Blumenthal & Koch

[57] ABSTRACT

Disclosed is a gas leak detector comprising; a tubular gas-sensitive element defining openings at both ends thereof, one end being a gas inlet and the other end a gas outlet, and made of an oxygen-ion conductive solid electrolyte; a set of electrodes provided respectively on the inner and outer walls of the gas-sensitive element, the electrode on the outer wall being kept in contact with a reference gas; a heater adapted to heat the gas-sensitive element to a predetermined temperature at a location corresponding to the set of electrodes; and a catalytic layer provided on the surface of the electrode on the inner wall being kept in contact with a target gas.

6 Claims, 7 Drawing Figures

GAS LEAK DETECTOR

BACKGROUND OF THE INVENTION

This invention relates to a gas leak detector, and more particularly to a gas leak detector capable of detecting a trace amount of gas leak from a variety of equipments, piping systems and the like and suitable for use in locating leak points.

Halogenated hydrocarbon gas has been widely used as refrigerant gas or coolant for electric refrigerators, air conditioners and the like. Halogenated hydrocarbon has a chemical formula wherein one or more of the hydrogen atoms has been replaced by chlorine, fluorine or the like, and typically includes R-12($CCl_2F_2$), R-22 ($CHClF_2$), etc. These halogenated hydrocarbons are chemically and thermally very stable, harmless to human bodies, and have excellent thermodynamical characteristics when they are used for refrigeration systems.

In the refrigeration systems, the halogenated hydrocarbon gas mentioned above is alternately compressed and expanded to cause its refrigeration actions. At this time, a trace amount of the halogenated hydrocarbon gas may sometimes leak away from compressors, radiators, pipes, etc. If such leaks are left unstopped, efficiency of the refrigeration systems is lowered due to a gradual decrease of the refrigerant gas, with the result of a possible cessation of the function of such equipment. Accordingly, stringent control is required when such equipment is manufactured in a factory, and it is desirable to periodically check any leak along the pipe systems. Especially, in the refrigeration systems such as air conditioners for cars and the like, there is a greater possibility of leak due to a shock during drive, and a detector which may simply find out the leaks has long been desired.

Generally, the air conditioner as mentioned above is heavy in weight, and in addition it is usually fixed at one place or mounted on a car. Therefore, it is impossible to make an inspections thereof by simply turning or overturning it. Moreover, the leaks are usually too small to find out visually or by a magnifier. Further, it is desirable for a leak detector to be as miniature as possible since the pipe system, etc. is usually of complicated structure. Still further, the detecting end of a detector should preferably be as small as possibile in diameter since the detector traces the pipe or the like to locate a leak. In addition, it is required that a detector can be operated by means of a miniature cell or cells in order to make it easy to handle. While the sensitivity of a detector is desirably as high as possible as a matter of course, it is required for it to detect a gas leak of at least $10^{-4}$ cc/sec (25° C., 1 atm).

There has been proposed a number of halogenated hydrocarbon gas detectors, some of examples of which are explained below:

A typical detector, a torch, utilizes a kind of flame reaction; it utilizes the phenomenon that the color of flame changes responding to the chemical reaction of the halogen gas mixed into the flame with a copper metal provided in the flame. Although this method is simple, it is often accompanied by errors because the presence or absence of leaks is visually judged. Moreover, the limit of detection according to this method is $10^{-2}$ cc/sec (25° C., 1 atm) at best.

Further, there has been proposed a detector which utilizes high voltage electric discharge. This detector is provided with a pair of electrodes exposed to air with a gap therebetween, to which electrodes is applied a high voltage of several hundred volts for producing an electric discharge at the gap. The discharge stops when halogenated hydrocarbon gas comes into the gap between the electrodes. As a result, the leak can be detected by detecting the change of the discharged current, with the detection limit leveled up to $10^{-3}$ cc/sec (25° C., 1 atm) which is sufficient for practical use. However, this detector, which utilizes the electric discharge, is disadvantageous in for example that the discharge is interrupted due to other external causes such as wind or the like even when there is no leak of the halogenated hydrocarbon gases.

On the other hand, as a detector having sufficiently high sensitivity, there has been known a detector called a cation emission type leak detector. The detector of this type comprises ceramics containing Na, K, etc., an ion collector electrode and a heater. The ceramics are heated to a high temperature (e.g. 800° C.), to which ceramics there is provided at a predetermined space an ion collector electrode made of a metal. While a high voltage of about 300 V is applied to the space between the ceramics and the ion collector electrode, the halogenated hydrocarbon gas is reacted on the surface of the ceramics due to the high temperature to emit ions of Na, K, etc. contained in the ceramics, which ions are attracted to and captured by the metallic electrode with the aid of the high voltage. As the result, the leak can be detected by detecting ionic current thus generated. According to this detector, the detection limit is not more than $10^{-6}$ cc/sec (25° C., 1 atm) and thus the detector exhibits very high sensitivity.

However, the detector of this type consumes the electric power of as large as 20~30 W because the ceramics must be kept at a high temperature (about 800° C.) as mentioned above, whereby not only a larger size of an apparatus but also a cord for the power source are required, and also the detector must be of a larger size for the same reason. In addition, such a detector is necessarily expensive because a metal such as platinum which is resistant to a high temperature must be generally used as the material for an electrode.

As a gas leak detector making use of an oxygen-ion conductive solid electrolyte, there has been known a gas leak detector in which a pair of electrodes are provided respectively on both surfaces of a plate-like oxygen ion conductive solid electrode and a porous oxydizing catalyst which can oxidize flammable gases such as CO gas, propane gas and the like, is applied on the surface of one of the electrodes (Japanese Patent Laidopen Application No. 146,690/1979). The aforementioned gas leak detector is certainly effective in finding an average gas concentration in the surrounding atmosphere, but it is extremely difficult for such a conventional gas leak detector to detect gas leakage, particularly, from a minute crack or hole.

SUMMARY OF THE INVENTION

With the foregoing in view, an object of this invention is to provide a small but high performance gas leak detector.

According to the present invention, there is provided a gas leak detector comprising;

a tubular gas-sensitive element defining openings at both ends thereof, one end being a gas inlet and the other end a gas outlet, and made of an oxygen-ion conductive solid electrolyte;

a set of electrodes provided respectively on the inner and outer walls of the gas-sensitive element, the electrode on the outer wall being kept in contact with a reference gas;

a heater adapted to heat the gas-sensitive element to a predetermined temperature at a location corresponding to the set of electrodes; and a catalytic layer provided on the surface of the electrode on the inner wall being kept in contact with a target gas.

BRIEF DESCRIPTION OF THE DRAWINGS

This invention will be described in detail below with reference to the accompanying drawings, in which.

DETAILED DESCRIPTION OF THE PREFERRED EMBODIMENTS

Figure 1:
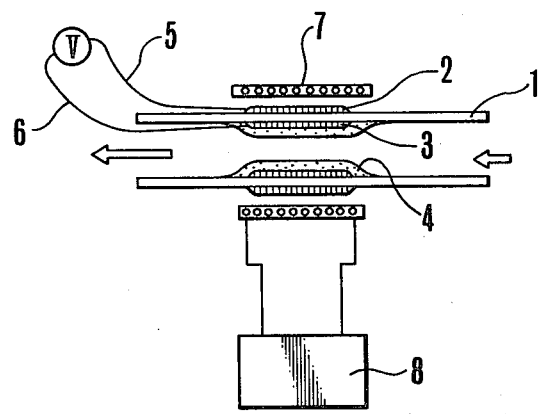
FIG. 1 is a schematic cross-sectional view of a gas leak detector according to an embodiment of this invention.

In this invention, as illustrated cross-sectionally in FIG. 1, electrodes 2, 3 are provided in pairs respectively on the outer and inner walls of a tubular oxygen-ion conductive solid electrolyte 1 which is principally made of $ZrO_2$, for example, $ZrO_2$-$Y_2O_3$ or $ZrO_2$-$CaO$ system. Of the electrodes 2 and 3, the surface of the electrode 3 provided on the inner wall is applied with a catalytic layer 4 comprising, for example, $V_2O_5$-$MoO_3$ supported on $\gamma$-$Al_2O_3$.

Incidentally, a suitable catalytic system may be readily selected depending on the type of a gas to be detected. In the case of detecting leak of a halogenated hydrocarbon gas represented by $CCl_2F_2$, $CHClF_2$ or the like, use of the aforementioned $V_2O_5$-$MoO_3$ supported on $\gamma$-$Al_2O_3$ promises excellent selectivity to the target gas because the oxygen-ion conductive solid electorolyte will develop electromotive forces of the opposite polarity than when brought into contact with other organic gases such as CO, $C_2H_5OH$ and the like.

When the above-mentioned catalytic layer formed of $V_2O_5$-$MoO_3$ supported on $\gamma$-$Al_2O_3$ is employed, it is preferred to use vanadium (V) in an amount ranging from 0.1 to 50 wt % of the $\gamma$-$Al_2O_3$ support and molybdenum (Mo) in such an amount as to make the atomic ratio of molybdenum to vanadium be 0.05~0.5. Extremely high sensitivity is available particularly when V=10 wt % and Mo/V=1/10.

Using, as an example, a catalyst formed of $V_2O_5$-$MoO_3$ supported on $\gamma$-$Al_2O_3$, various gases were brought into contact with an oxygen-ion conductive solid electrolyte to determine the polarities of the thus-developed electromotive forces. Results are shown in the following table.

|  | Air | $CCl_2F_2$ | $CHClF_2$ | $CHCCl_3$ | CO | $C_2H_5OH$ | $C_4H_{10}$ | Gasoline |
|---|---|---|---|---|---|---|---|---|
| Outer Electrode | − | − | − | − | + | + | + | + |
| Inner Electrode | − | + | + | + | − | − | − | − |

On the other hand, the oxygen partial pressure on the electrode 2 provided on the outer wall of the oxygenion conductive solid electrolyte remains practically constant since the electrode 2 is in direct contact with the atmosphere without catalytic layer.

Namely, in a gas leak detector according to this invention, a target gas is subjected to decomposition upon contact with the catalytic layer 4 while it is introduced into the hollow part of the tubular oxygen-ion conductive solid electrolyte and then charged out of the hollow part. Here, the decomposition results in the consumption of at least a part of oxygen in air, which has been introduced together with the target gas, and oxygen which has been adsorbed in the catalytic layer and porous electrode, thereby leading to a lowered oxygen partial pressure in the vicinity of the electrode on the inner wall of the solid electrolyte.

As a result, a difference in oxygen partial pressure arises between the electrode 3 on the inner wall and the electrode 2 on the outer wall, thereby generating an electromotive force.

The heater 7 may be of any type so long as it can heat the oxygen-ion conductive solid electrolyte to a predetermined temperature. It may for example be arranged near the outer circumference of the detector as illustrated in FIG. 1. Alternatively, it may be provided within the hollow part of the tubular oxygen-ion conductive solid electrolyte (not shown). It is however preferable, from the practical viewpoint, to provide the heater on the surface of the electrode on the outer wall by burying the heater in an inorganic cement containing principally at least one of aluminum phosphate and sodium silicate. Use of aluminum phosphate and/or sodium silicate as cement is advantageous because it exhibits excellent adhesiveness to the electrode on the outer wall (or the oxygen-ion conductive solid electrolyte) upon coating same, it is converted to a porous structure having superior gas permeability after dried and sintered, and it maintains a high degree of adhesive strength stably.

On the other hand, the electrode on the outer wall of the tubular oxygen-ion conductive solid electrode, which electrode is brought into contact with a reference gas in the present invention, can be usually maintained in an exposed state to air as shown in FIG. 1. Namely, when comparing the oxygen partial pressure in the interior of the tubular electrolyte with that outside the same tubular electrolyte (i.e., in the atmosphere) as in the present invention, the electrode outside the tubular electrolyte is substantially free from the influence of each target gas. Therefore, the surrounding atmosphere of air may be utilized as the reference gas. If a still higher degree of sensitivity is desired, it may be effective to provide a cover 10 as cross-sectionally depicted in FIG. 2 so as to prevent the electrode 2 on the outer wall from being in direct contact with the target gas. Incidentally, the cover 10 may be made of any material such as metal, ceramics or the like so long as the material does not affect adversely on the detection of gas leak. It may be of any configurations suitable to avoid or suppress the direct contact of the target gas to the electrode 2 on the outer wall.

Preferred embodiments of this invention will hereinafter be described by the following Examples:

EXAMPLE 1

In the structure illustrated as a cross-sectionally in FIG. 1, $ZrO_2$ containing 5~8 mol % of $Y_2O_3$ was used as the oxygen-ion conductive solid electrolyte 1. Platinum paste was baked on the electrodes 2, 3 and a catalytic system of the $V/Al_2O_3$ weight ratio of 1/10 and the V/Mo atomic ratio of 1/10 was applied as the catalytic layer 4 on the surface of the electrode 3 on the inner wall. The thus-fabricated detector was heated to about 450° C. to determine the detectable lower concentration limit for each of $CCl_2F_2$ and $CHClF_2$ as halogenated hydrocarbon gases.

Figure 3:
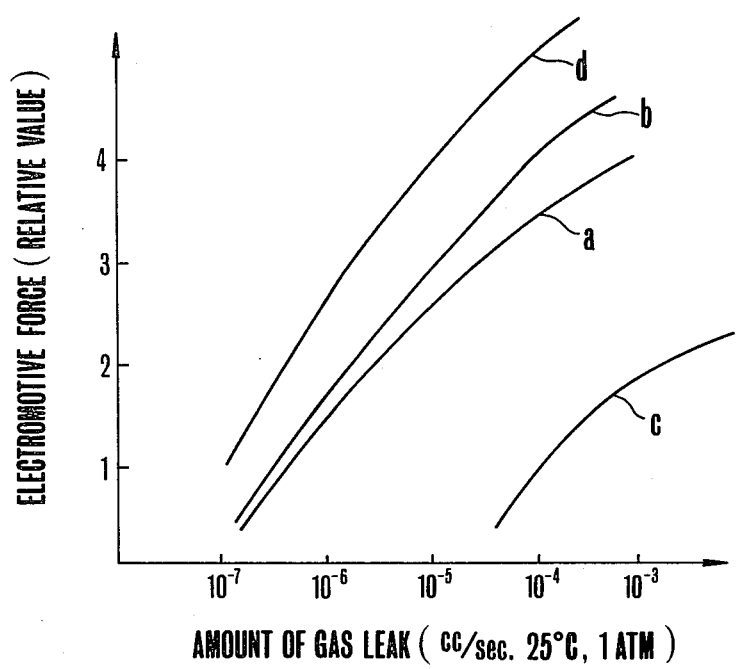
FIG. 3 diagrammatically depicts variation in electromotive force developed by each of four different gas leak detectors at varied rates of leak of a target gas.

As readily envisaged from FIG. 3, the detectable lower concentration limit for $CCl_2F_2$ (represented by the curve a) was $6\times10^{-6}$ cc/sec. On the other hand, $CHClF_2$ had the detectable lower concentration limit at $8\times10^{-6}$ cc/sec. (not shown in the diagram).

COMPARATIVE EXAMPLE 1

Figure 4:
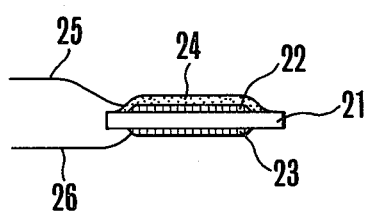
FIG. 4 is a schematic cross-sectional view of a conventional gas leak detector.

A gas leak detector having a prior art structure was also fabricated for the sake of comparison. Namely, as shown cross-sectionally in FIG. 4, electrodes 22, 23 were provided respectively on both surfaces of an oxygen-ion conductive solid electrolyte 21 and a catalytic layer 24 was applied on the surface of the electrode 22. A measurement was carried out with the gas leak detector in the same manner as in Example 1. Measurement results are represented by the curve c in FIG. 3.

EXAMPLE 2

Figure 2:
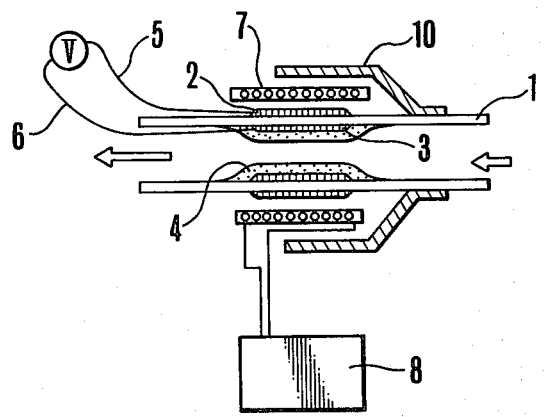
FIG. 2 is a schematic cross-sectional view of a gas leak detector according to another embodiment of this invention.
Figure 5:
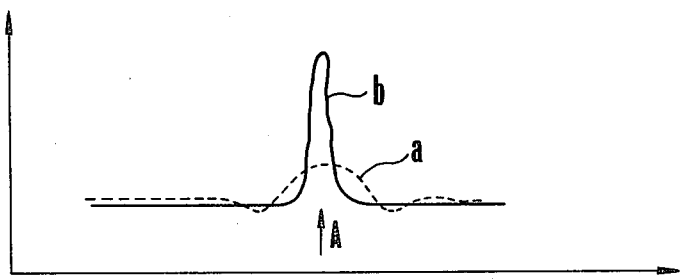
FIG. 5 is a diagrammatic illustration of the relationship between the distance from a leak point and the voltage level developed.

As illustrated in FIG. 2, a metallic cover 10 was provided with the detector of Example 1 so as to minimize the chance of the target gas to be brought into contact with the electrode 2 on the outer wall. The thus fabricated gas leak detector showed the same sensitivity as represented by the curve b in FIG. 3 when the detector was used in a stational state as in Example 1. However, distinct differences arose in both sensitivity and resolving power between the detector of Example 1 and that of the present example when the detector was scanned along a carrier pipe to suck the target gas as indicated by arrows in FIGS. 1 and 2. Results of the above experiment are shown in FIG. 5, in which output signals produced upon contact with the target gas are plotted along the vertical axis while various points along the carrier pipe for the target gas are plotted along the horizontal axis. Letter A indicates the point of gas leak. In FIG. 5, the curve a represents obtained using the detector of Example 1 and the curve b shows measurement results obtained with the detector of Example 2.

As apparent from the above results, both output and resolving power upon detecting gas leak are improved by the provision of the cover 10 as in Example 2.

EXAMPLE 3

Figure 6:
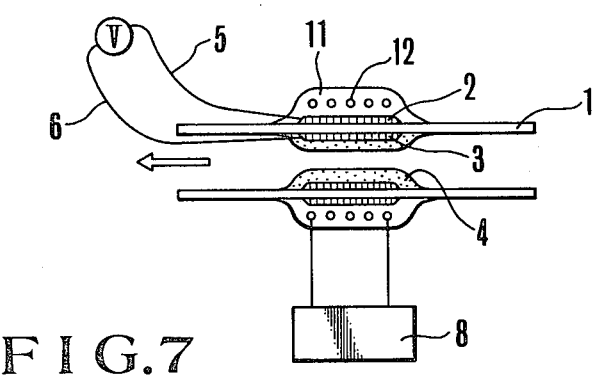
FIG. 6 is a schematic cross-sectional view of a gas leak detector according to a further embodiment of this invention.

As cross-sectionally illustrated in FIG. 6, a gas leak detector of the same structure as that shown in FIG. 1 was fabricated by providing a heater 12 on the outer surface of the detector in such a fashion that it was buried in an inorganic cement 11 consisting principally of at least either one of aluminum phosphate and sodium silicate. The thus-fabricated detector showed the same sensitivity as the detector of Example 1. It exhibited excellent physical strength, notably superior resistance to vibrations when employed at high temperatures.

EXAMPLE 4

Figure 7:
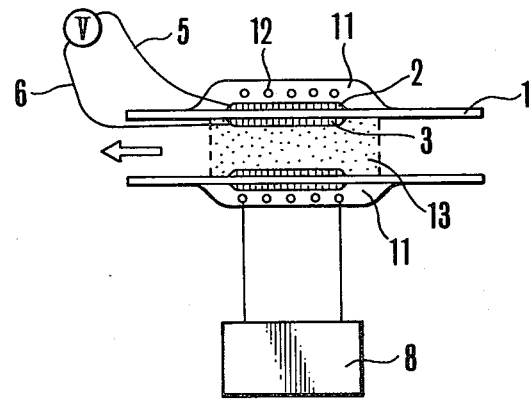
FIG. 7 is a schematic cross-sectional view of a gas leak detector according to a still further embodiment of this invention.

As cross-sectionally shown in FIG. 7, the detector of Example 3 was provided with a catalytic layer 13 by packing the same catalyst as that employed in Example 1 in a hollow space corresponding to the electrode 3 on the inner wall. The thus-fabricated detector showed better detection sensitivity than the detector of Example 3, as indicated by the curve d in FIG. 3. However, it required somewhat longer response time.

Needless to say, the cover, heater, catalytic layer and other components or parts of the gas leak detector according to this invention can be modified in configurations, materials, etc. as desired.

We claim:
1. A process for the differential detection of halogenated hydrocarbon gas, comprising the steps of:
    (1) providing a tubular, oxygen-ion conductive, solid electrolyte comprising $ZrO_2$, said tubular electrolyte defining an inner wall and an outer wall;
    (2) providing a first electrode on said inner wall and a second electrode on said outer wall, the surface of said first electrode being coated with a catalytic layer comprising $V_2O_5$-$MoO_3$ supported on α-$Al_2O_3$;
    (3) exposing only said first electrode to a test gas in said tubular, oxygen ion-conductive, solid electrolyte, said test gas containing either a halogenated or a nonhalogenated hydrocarbon
    (4) detecting the presence of said halogenated hydrocarbon in said test gas by measuring a polarity at said first electrode relative to said second electrode which is opposite to a polarity measured when said test gas contains said nonhalogenated hydrocarbon.
2. A device for the differential detection of halogenated hydrocarbon gas comprising:
    a tubular gas-sensitive element defining openings at both ends thereof, one end bearing a gas inlet and the other end a gas outlet, and made of an oxygen-ion conductive solid electrolyte comprising $ZrO_2$;
    a set of electrodes provided respectively on the inner and outer walls of the gas-sensitive element, the electrode on the outer wall being kept in contact with a reference gas;
    a heater adapted to heat the gas-sensitive element to a predetermined temperature at a location corresponding to the set of electrodes; and
    a catalytic layer formed of $V_2O_5$-$MoO_3$ supported on α-$Al_2O_3$ and covering directly the surface of the electrode on the inner wall being kept in contact with a target gas.

3. The device according to claim 1, wherein said catalytic layer comprises vanadium in an amount of from 0.1 to 50 wt % of the γ-Al$_2$O$_3$ support and molybdenum in such an amount as to make the atomic ratio of molybdenum to said vanadium be 0.05 to 0.5.

4. The device according to claim 1, wherein a cover is provided on the outer surface of the gas-sensitive element so as to prevent the outer electrode from being in direct contact with the target gas.

5. The device according to claim 1, wherein said heater to provided on the outer electrode by burying it in an inorganic cement containing principally at least one of aluminum phosphate and sodium silicate.

6. The device according to claim 1, wherein said catalytic layer is formed by packing the catalyst in a hollow space corresponding to the inner electrode.

* * * * *